ions found in the use of prior art prosthetic valves. The heart valve is a trileaflet type which has its formed leaflets heat set in a partially open position to reduce pressure required to open the leaflets in response to blood flowing therethrough.

United States Patent [19]
Pierce et al.

[11] 4,364,127
[45] Dec. 21, 1982

[54] TRILEAFLET TYPE PROSTHETIC HEART VALVE

[75] Inventors: William S. Pierce, Hummelstown; Craig B. Wisman, Harrisburg; James H. Donachy, Annville, all of Pa.

[73] Assignee: Research Corporation, New York, N.Y.

[21] Appl. No.: 308,168

[22] Filed: Oct. 2, 1981

[51] Int. Cl.³ ............................................. A61F 1/22
[52] U.S. Cl. ................................. 3/1.5; 29/157.1 R; 137/849; 264/299; 264/320
[58] Field of Search ..................... 3/1.5; 137/844, 849; 264/299, 320; 29/458, 460, 157.1 R

[56] References Cited
U.S. PATENT DOCUMENTS

| | | | |
|---|---|---|---|
| 2,822,819 | 2/1958 | Geeraert | 137/844 |
| 3,320,972 | 5/1967 | High et al. | 3/1.5 X |
| 3,445,916 | 5/1969 | Schulte | 3/1.5 X |
| 3,548,417 | 12/1970 | Kischer | 3/1.5 |
| 3,655,306 | 4/1972 | Ross et al. | 3/1.5 X |
| 3,710,744 | 1/1973 | Goodenough et al. | 3/1.5 X |
| 3,717,883 | 2/1973 | Mosher | 3/1.5 |
| 3,744,062 | 7/1973 | Parsonnet | 3/1.5 |
| 3,755,823 | 9/1973 | Hancock | 3/1.5 |
| 4,222,126 | 9/1980 | Boretos et al. | 3/1.5 |

Primary Examiner—Ronald L. Frinks
Attorney, Agent, or Firm—Kerkam, Stowell, Kondracki & Clarke

[57] ABSTRACT

A prosthetic heart valve constructed of hemo-compatible materials that is anatomically and functionally similar to the natural aortic valve is disclosed which reduces or eliminates the occurrence of many of the complications found in the use of prior art prosthetic valves. The heart valve is a trileaflet type which has its formed leaflets heat set in a partially open position to reduce pressure required to open the leaflets in response to blood flowing therethrough.

6 Claims, 12 Drawing Figures

TRILEAFLET TYPE PROSTHETIC HEART VALVE

TECHNICAL FIELD

This invention is directed to an improved trileaflet type prosthetic heart valve and to a method of making same.

BACKGROUND OF THE PRIOR ART

Cardiac surgeons first began to attempt operative correction of valvular lesions of the heart in the late 1940's. At that time adequate results could not be achieved by the then-available repair or reconstructive procedures, and it became evident that a replacement for the diseased natural valve was required. Work in the early 1950's focused on the descending aorta ball valve and the first successful placement of a prosthetic cardiac valve in a normal anatomical position occurred in March of 1960. Since that time, many investigators have grappled with the design and evaluation problems associated with prosthetic heart valves. A myriad of designs have come and gone but relatively few such designs enjoy clinical popularity at this time. Significant postoperative problems accompany even the best valves now available and the search for a prosthetic valve with better function and decreased incidence of complications continues.

Currently available valve prostheses are of two types; trileaflet valves fabricated from biological tissues or man-made mechanical valves. The biological valves have a tendency for failure due to stiffening and calcification of the leaflets while the mechanical valves have a tendency to cause dangerous clot formation at hinge points. Moreover, many of these mechanical valves have an unacceptably high opening pressure gradient. The present invention features the low opening pressure gradient and freedom from clot formation of the biological trileaflet valves combined with the durability of a mechanical valve.

The following U.S. Patents disclose various forms of construction of trileaflet type prosthetic heart valves:

| Inventor | Pat. No. |
| --- | --- |
| Geeraert | 2,822,819 |
| High et al | 3,320,972 |
| Schulte | 3,445,916 |
| Parsonnet | 3,744,062 |
| Hancock | 3,755,823 |
| Boretos et al | 4,222,126 |

Many manifestations of valvular disease of the heart are presently amenable to correction by the use of a prosthetic device to simulate the hemodynamic functioning of a natural valve. However, presently available valvular prostheses do not simulate the anatomic functioning of the natural valve and indeed, flow characteristics are generally far from that seen in the natural valve. As a consequence of the departure from the natural state, postoperative complications appear. These complications can be classified into five major areas: thromboembolic; functional; technical; anatomical; and hemolysis.

BRIEF SUMMARY OF THE INVENTION

It is an object of the present invention to provide a prosthetic valve using proven hemo-compatible materials that is anatomically and functionally similar to the natural aortic valve, to thereby reduce or eliminate the occurrence of many of the complications found in the use of prior art prosthetic heart valves.

The present invention may be generally defined as comprising a trileaflet heart valve including:

1. a frame consisting of a ring shaped base with three upstanding struts, which struts taper in thickness from the base to thin tips and the base is provided with a hemicylindrical groove in its external surface to receive a thin fabric or the like suture attachment element; and 2. a one piece plastic membrane which forms the three leaflets of the valve; the formed leaflets are heat set in a partially open position to reduce the pressure required to open the leaflets by blood flowing through the prosthetic valve.

The above defined invention provides a heart valve that has a low pressure gradient, low tendency for clotting and a long functional life.

The low pressure gradient is a result of the thin leaflets and the heat set central opening. The low tendency for clotting is a result of the one piece, seam free surfaces that the valve presents to the blood stream. The long functioning life is related to the inert polyurethane leaflets, the interleaflet coaptation zone that allows each closed leaflet to support the adjacent ones and the tapered, flexible posts of the stent, which allow part of the closing forces to be absorbed by the stent, rather than solely by the junction of the leaflet and the stent.

BRIEF DESCRIPTION OF THE DRAWINGS

The invention will be more particularly described in reference to the accompanying drawing wherein.

DETAILED DESCRIPTION OF THE INVENTION

Figure 1:
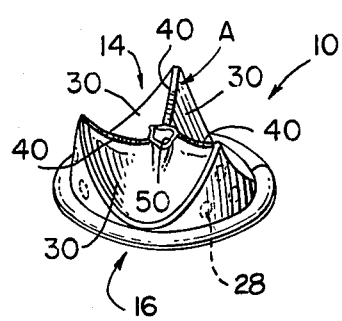
FIG. 1 is a perspective view of a heart valve constructed in accordance with the teachings of the present invention.

Referring to FIGS. 1 through 4 of the drawing, the prosthetic heart valve is generally designated 10 and includes a stent portion 12, a trileaflet valve portion 14 and a suture receiving element generally designated 16.

The stent 12 is constructed preferably of a biocompatible relatively rigid plastic composition such as the polyurethanes, polycarbonates and the polypropylenes. The stent includes a base portion 18 of cylindrical configuration, which base portion has formed integrally therewith three upstanding struts positioned 120° on center in respect to the base which struts are designated 20.

The cylindrical base portion has molded or machined therein a groove 22 which groove supports the suture receiving ring to the stent.

Figure 3:
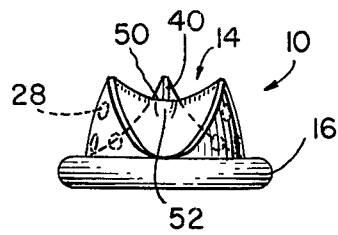
FIG. 3 is a side elevational view of the structures illustrated in FIGS. 1 and 2.
Figure 4:
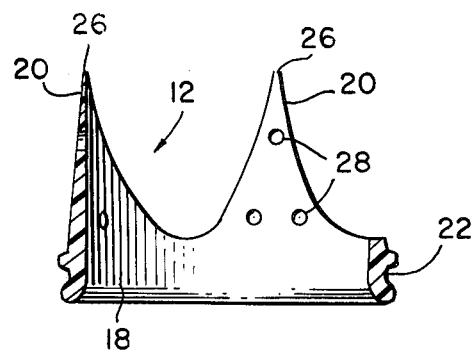
FIG. 4 is a section through the stent with the section corresponding to line 4—4 of the heart valve illustrated in FIG 2.
Figure 5:
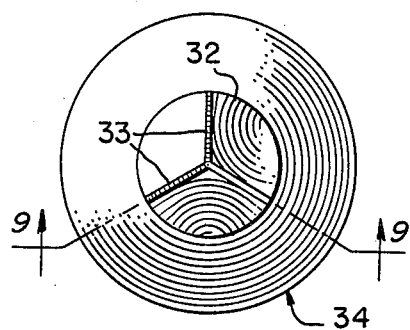
FIG. 5 is a top plan view of a former shaped to receive the stent and to provide support for the plastic leaflets during formation thererof.
Figure 6:
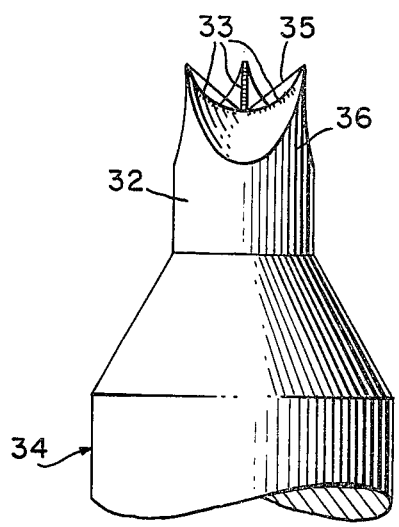
FIG. 6 is a side view of the former illustrated in FIG. 5.

It will be particularly noted from FIG. 4 that the struts taper in thickness from a thicker base to thinner tips 26 to provide variable flexibility from the base to the tips for each of the struts to decrease the closing forces on the leaflets 14. Further to improve the anchoring of the plastic composition forming the trileaflets of the prosthetic valve a number of openings are molded or bored, such as at 28, in each of the struts as illustrated in dotted lines in FIGS. 1 and 3 and full lines in FIG. 4. Suitable dimensions for the stent for an adult human would be: height of stent, 0.50"; internal diameter of stent at base 0.90"; height of base portion 0.150"; height of retaining groove 0.10"; thickness of the struts at the tip end 0.030"; thickness of the stent at the base portion 0.17" and diameter of membrane retaining openings 0.075".

While the foregoing dimensions have been given by way of illustration, the dimensions would be varied depending on the size of the valve to be replaced and the actual material of construction of the stent.

It will be particularly noted from FIG. 4 of the drawing that the struts 20 are positioned and shaped to provide support for the three leaflets 30 forming the skin or membrane portion 14 of the improved prosthetic heart valve.

After the stent has been formed either by casting, molding, machining, molding and machining, etc., the stent is coated with a biocompatible, curable plastic composition. The material chosen for this coating and for formation of the membrane is preferably segmented polyurethane which has been shown to be equal or superior to medical grade silicone rubber in terms of hemo-compatibility and to be far superior to other biocompatible materials in mechanical and durability qualities. Further, segmented polyurethane can be used to create complex shapes on reasonably simple molds by a dipping process.

Figure 9:
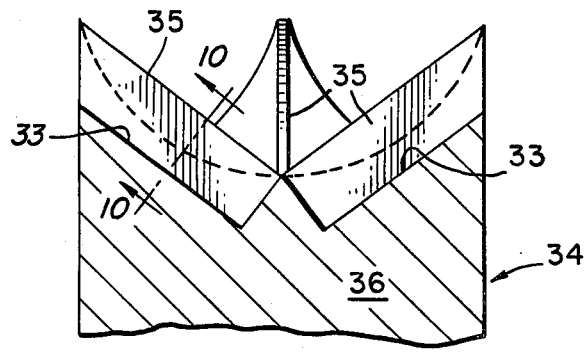
FIG. 9 is a greatly enlarged, fragmentary sectional view on line 9—9 of FIG. 5 illustrating the three shims mounted in the former.
Figure 10:
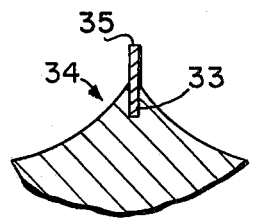
FIG. 10 is a fragmentary sectional view on line 10—10 of FIG. 9.
Figure 11:
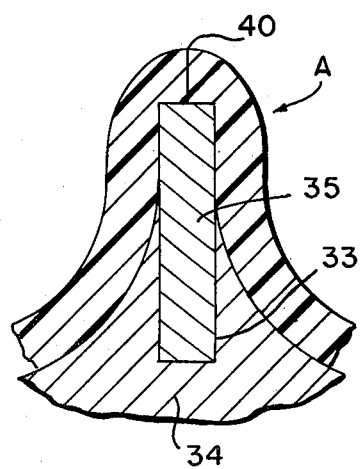
FIG. 11 is a greatly enlarged fragmentary sectional view like FIG. 10 with a portion of the leaflet's membrane prior to cutting the membrane along the coaptation zone.
Figure 12:
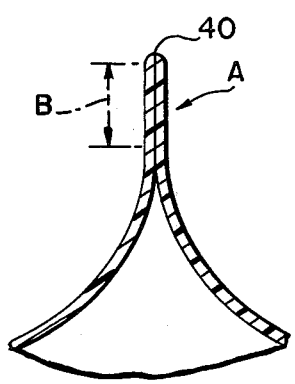
FIG. 12 illustrates the portion of the membrane shown in FIG. 11 after the valve has been removed from the membrane forming form and after the membrane has been separated along a coaptation line.

In order to form the membrane for the valve, the coated stent is slipped over the end portion 32 of a form 34 illustrated, for example, in FIGS. 5, 6, 9, 10 and 11. The stent is positioned on the form stem 32 with each of the struts 20, FIG. 4, of the stent aligned with elements 36 on the form. In order to achieve a coaptation zone A, FIG. 12, between adjacent leaflets along lines 40, FIGS. 1 2, 11 and 12 the form 34 contains 0.005" wide grooves 33 into each of which is fitted a rectangular piece of stainless steel shim stock 35, FIGS. 9–11. A small segment of the shims 35 protrudes above the grooves 33 a maximum of about 0.125" as best illustrated in FIGS. 9 and 10. After positioning of the coated stent on the form 34, having the shims 35 in place, the upper portion of the form is dipped in an uncured segmented polyurethane, much as in the early candle making art and the coated structure, is permitted to cure and redipped alternately until a layer of the polyurethane of the desired thickness is provided. A membrane thickness on the order of 0.006" to about 0.008" has been found to provide the proper leaf flexibility and durability. Following final curing of the dipped stent, the stent with the leaves formed thereon is removed from the form 34. Thereafter the leaves are separated by carefully cutting along the top edge of the coaptation zones A, formed by the shims 35, FIGS. 11 and 12. After being cut, the membranes at the coaptation zones, present flat surfaces of contact rather than lines of contact as illustrated at B in FIG. 12. Thus on closing the three leaves tend to support each other. The formed coaptation zone would have a maximum height in the order of about 0.125 inch.

Figure 7:
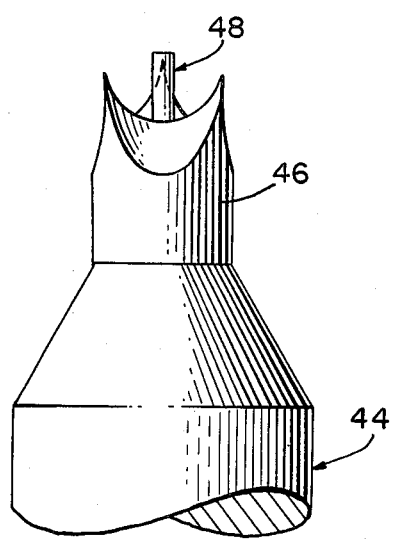
FIG. 7 is a side view of a heat setting form adapted to receive the heart valve at the time of heat setting.
Figure 8:
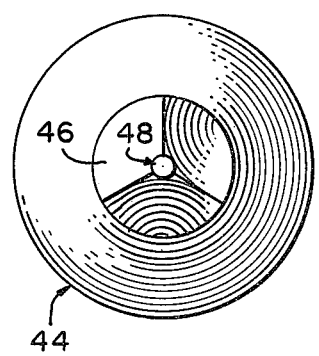
FIG. 8 is a top plan view of the structure illustrated in FIG. 7.

The next step in forming the completed prosthetic valve is to place the valve on a second form 44, shown in FIGS. 7 and 8 having a tip portion 46 sized to receive the coated stent. It will be noted that the form 44 is provided with an upstanding former of cylindrical configuration generally designated 48.

Figure 2:
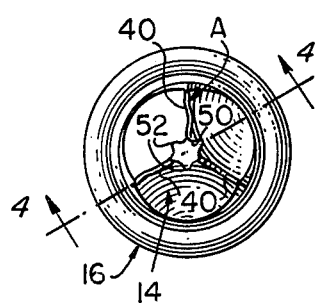
FIG. 2 is a top plan view of the structures illustrated in FIG. 1.

After the three leaves of the molded valve have been severed as hereinbefore described, the stent with the membrane covering, is placed on form 44 with the pin 48 projecting through the leaves. With the valve in this position, it is subjected to heat setting conditions appropriate for the particular plastic material. Where the membrane is segmented polyurethane temperatures in the order of from about 270° F. to about 280° F. for a period of about 45 to about 60 minutes have been found to be sufficient to properly heat set the valve so that when the valve is in its relaxed condition, a center opening 50, FIGS. 1, 2 and 3 is provided in the valve. It will be noted that small pleats 52 appear in the surface of the membrane to form the heat set opening. In the case of a trileaflet valve three such pleats 52 would appear.

It has been determined that where the pin 48 has a diameter of about 0.125" to about 0.140", it only requires a back pressure of about 1 mm of mercury to completely close the opening. In flow testing of the valve very little regurgitation of blood would result from the heat set opening whereas reduction in pressure loss in completely opening the valve far overshadows any regurgitation losses.

The final step is fabrication of the valve is the placement of the suture ring 16 in the groove 22.

We claim:

1. A prosthetic trileaflet type heart valve comprising:
   1. a frame having a ring shaped base and three upstanding struts;
   said base further provided with a groove in its external surface to receive a thin fabric or the like suture element;
   2. a one piece membrane formed on said frame to provide three leaflets of the valve;
   said formed leaflets being heat set in a partially open position to reduce the pressure required to open the leaflets by blood flowing through the prosthetic valve.

2. The prosthetic trileaflet type heart valve as defined in claim 1 wherein the frame comprises polycarbonate, polypropylene or polyurethane and the membrane comprises segmented polyurethane.

3. A prosthetic trileaflet type heart valve comprising:

1. a frame having a ring shaped base and three upstanding struts, which struts taper in thickness from the base to thin tips;

said base further provided with a hemicylindrical groove in its external surface to receive a thin fabric or the like suture element;

2. a one piece plastic membrane forming three leaflets of valve; the formed leaflets are heat set in a partially open position to reduce the pressure required to open the leaflets by blood flowing through the prosthetic valve.

4. A prosthetic trileaflet type heart valve as defined in claims 1 or 3 wherein each leaflet is formed with a coaptation zone with adjacent leaflets.

5. A method of making a prosthetic trileaflet type heart valve comprising:

1. forming a frame consisting of a ring shaped base with three upstanding struts, which struts taper in thickness from the base to thin tips;

2. forming on the frame a one piece plastic membrane which forms the three leaflets of the valve;

3. heat setting the formed leaflets in a partially open position to reduce the pressure required to open the leaflets by blood flowing through the prosthetic valve.

6. A method of making a prosthetic trileaflet type heart valve comprising:

1. forming a frame consisting of a ring shaped base with three upstanding struts, which struts taper in thickness from the base to thin tips;

2. forming in the base a hemicylindrical groove in its external surface to receive a thin fabric or the like suture element;

3. forming on the frame a one piece plastic membrane which forms the three leaflets of the valve;

4. heat setting the formed leaflets in a partially open position to reduce the pressure required to open the leaflets by blood flowing through the prosthetic valve.

* * * * *